| (12) | United States Patent | (10) Patent No.: | US 9,147,267 B2 |
|---|---|---|---|
| | Bruder et al. | (45) Date of Patent: | Sep. 29, 2015 |

(54) RECONSTRUCTION OF IMAGE DATA

(71) Applicants: Herbert Bruder, Höchstadt (DE);
Rainer Raupach, Heroldsbach (DE)

(72) Inventors: Herbert Bruder, Höchstadt (DE);
Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 313 days.

(21) Appl. No.: 13/674,422

(22) Filed: Nov. 12, 2012

(65) Prior Publication Data

US 2013/0121555 A1     May 16, 2013

(30) Foreign Application Priority Data

Nov. 16, 2011  (DE) .................. 10 2011 086 456

(51) Int. Cl.
  *G06K 9/00* (2006.01)
  *G06T 11/00* (2006.01)
  *A61B 6/03* (2006.01)
  *A61B 6/00* (2006.01)

(52) U.S. Cl.
  CPC ............. *G06T 11/003* (2013.01); *G06T 11/006* (2013.01); *A61B 6/032* (2013.01); *A61B 6/5205* (2013.01); *G06T 2211/424* (2013.01)

(58) Field of Classification Search
  None
  See application file for complete search history.

(56) References Cited

U.S. PATENT DOCUMENTS

| 5,432,866 | A | * | 7/1995 | Sakamoto | 382/128 |
|---|---|---|---|---|---|
| 5,774,572 | A | * | 6/1998 | Caspi | 382/141 |
| 6,631,198 | B1 | * | 10/2003 | Hannigan et al. | 382/100 |
| RE38,716 | E | * | 3/2005 | Caspi et al. | 382/141 |
| 7,313,214 | B2 | * | 12/2007 | Bruder et al. | 378/15 |
| 7,650,023 | B2 | | 1/2010 | Fischer et al. | |
| 7,773,787 | B2 | * | 8/2010 | Tek et al. | 382/128 |
| 7,860,208 | B2 | * | 12/2010 | Haerer et al. | 378/7 |
| 7,899,229 | B2 | * | 3/2011 | Luo et al. | 382/128 |

(Continued)

FOREIGN PATENT DOCUMENTS

| DE | 102004017538 A1 | 11/2005 |
|---|---|---|
| DE | 102004008979 B4 | 12/2006 |

(Continued)

OTHER PUBLICATIONS

Pietro Perona et al.; "Scale-Space and Edge Detection Using Anisotropic Diffusion", IEEE Transactions on Pattern Analysis and Machine Intelligence, vol. 12, No. 7, Jul. 1990, pp. 629 to 639; Others; 1990.

(Continued)

*Primary Examiner* — Chan Park
*Assistant Examiner* — Iman K Kholdebarin
(74) *Attorney, Agent, or Firm* — Harness, Dickey & Pierce, P.L.C.

(57) ABSTRACT

A method and image reconstruction facility are disclosed for reconstructing an image dataset based on a projection dataset acquired with the aid of an x-ray computed tomography apparatus. With an embodiment of the method, a first image dataset is reconstructed based on the projection dataset and an edge image dataset is generated, which indicates a measure of an edge strength of edges occurring in at least one spatial/temporal direction in the first image dataset, as a function of location. An output image dataset is then generated based on the first image dataset, with the resolution in the first image dataset being increased as a function of location in at least one spatial/temporal direction taking into account the edge image dataset.

21 Claims, 4 Drawing Sheets

(56) References Cited

U.S. PATENT DOCUMENTS

| | | | |
|---|---|---|---|
| 7,912,263 B2* | 3/2011 | Luo | 382/128 |
| 7,940,884 B2* | 5/2011 | Bruder et al. | 378/4 |
| 7,995,828 B2* | 8/2011 | Wang et al. | 382/132 |
| 8,483,515 B2* | 7/2013 | Matsunobu et al. | 382/299 |
| 8,830,398 B2* | 9/2014 | Inoue et al. | 348/558 |
| 8,867,831 B2* | 10/2014 | Mel et al. | 382/162 |
| 2004/0062341 A1* | 4/2004 | Popescu et al. | 378/4 |
| 2004/0234031 A1* | 11/2004 | Francke et al. | 378/98 |
| 2006/0002624 A1* | 1/2006 | Tamura | 382/266 |
| 2006/0204076 A1* | 9/2006 | Avinash et al. | 382/154 |
| 2007/0110300 A1* | 5/2007 | Chang et al. | 382/162 |
| 2008/0292171 A1* | 11/2008 | Bruder et al. | 382/131 |
| 2009/0034678 A1* | 2/2009 | Popescu | 378/10 |
| 2009/0041305 A1* | 2/2009 | Luo et al. | 382/107 |
| 2010/0027891 A1* | 2/2010 | Gwak et al. | 382/199 |
| 2010/0053349 A1* | 3/2010 | Watanabe et al. | 348/222.1 |
| 2010/0066874 A1* | 3/2010 | Ishiga | 348/252 |
| 2010/0280378 A1* | 11/2010 | Nakahira et al. | 600/445 |
| 2011/0052030 A1 | 3/2011 | Bruder et al. | |
| 2011/0188728 A1* | 8/2011 | Sammak et al. | 382/133 |
| 2011/0222783 A1* | 9/2011 | Matsunobu et al. | 382/218 |
| 2011/0246521 A1* | 10/2011 | Luo et al. | 707/776 |
| 2012/0027167 A1* | 2/2012 | O'Brien et al. | 378/20 |
| 2013/0076865 A1* | 3/2013 | Tateno et al. | 348/46 |
| 2013/0077860 A1* | 3/2013 | Peng et al. | 382/165 |
| 2013/0107120 A1* | 5/2013 | Inoue et al. | 348/558 |
| 2013/0301912 A1* | 11/2013 | Mel et al. | 382/162 |

FOREIGN PATENT DOCUMENTS

| | | |
|---|---|---|
| DE | 102007013417 A1 | 9/2008 |
| DE | 102009014726 A1 | 10/2010 |
| DE | 102009039987 A1 | 3/2011 |
| JP | 2011210253 A * | 10/2011 |

OTHER PUBLICATIONS

Jean-Baptiste Thibault et al, A three-dimensional statistical approach to improved image quality for multislice helical CT; Medical Physics, vol. 34, No. 11, Nov. 2007; Others; 2007.

H.Bruder, R.Raupach et al., "Reduction of radiation dose in CT with a FBP-based iterative reconstruction", Siemens AG Healthcare, Forchheim, Germany, ECR 2010; Others; 2010.

Joachim Weichert,"Anisotropic Diffusion in Image Processing", B.G. Teubner Stuttgart 1998, S. 1-184; Others; 1998.

German Office Action for German Application No. DE 10 2011 086 456.3 (Not Yet Published).

German Priority Document for German Application No. DE 10 2011 086 456.3 (Not Yet Published).

* cited by examiner

RECONSTRUCTION OF IMAGE DATA

PRIORITY STATEMENT

The present application hereby claims priority under 35 U.S.C. §119 to German patent application number DE 10 2011 086 456.3 filed Nov. 16, 2011, the entire contents of which are hereby incorporated herein by reference.

FIELD

At least one embodiment of the invention generally relates to a method for reconstructing an image dataset based on a projection dataset acquired using an x-ray computed tomography apparatus and/or to a method for generating image data of the interior of an object using an x-ray computed tomography apparatus, with which the reconstruction method is used. At least one embodiment of the invention also generally relates to an image reconstruction facility and an x-ray computed tomography apparatus for performing the method.

BACKGROUND

With an x-ray computed tomography method the object for which a projection dataset is to be acquired is generally exposed to x-ray radiation from a number of projection directions. An image dataset is then reconstructed from this projection dataset. This is generally done using a back projection method, in which in most instances the projection data acquired from the scanner of the x-ray computed tomography apparatus is preprocessed. A so-called rebinning step is then performed, in which the data generated with the beam propagated in the manner of a fan from the source is rearranged so that it is present in such a form as if the detector were struck by an x-ray beam wave front running in a parallel manner to the detector. The data that has been rearranged and filtered in this manner is then used for a back projection onto the individual image points within the volume of interest.

The standard method generally used here is a so-called filtered back projection method FBP. With this method the rebinned data is generally first transformed into the frequency range, where filtering takes place by multiplication using a convolution kernel. The filtered data is then back transformed and the back projection takes place with the filtered data. The selection of the convolution kernel allows the desired image characteristic, in particular the image sharpness and noise, to be influenced.

However such simple back projection methods have the disadvantage that the image sharpness is always linked to image noise. The greater the sharpness achieved, the greater the image noise and vice versa. Therefore iterative reconstruction methods have recently been developed, with which such limitations can be eliminated to some degree.

With such an iterative reconstruction method a reconstruction of initial image data from the measured projection data takes place first. A convolution back projection method for example can be used for this purpose. From this initial image data a "projector" (projection operator), which should map the measuring system mathematically as closely as possible, is then used to generate synthetic projection data. The difference in respect of the measurement signals is then back projected, thereby reconstructing a residue image, which can be used to update the initial image. The updated image data can in turn be used to generate new synthetic projection data in a next iteration step with the aid of the projection operator, to form the difference in respect of the measurement signals from this again and to calculate a new residue image, which can in turn be used to improve the image data of the current iteration stage.

Such a method allows image data to be reconstructed, which has relatively good image sharpness but still a low level of image noise. Such raw data-based or projection data-based iteration methods have the disadvantage of being very computation-intensive due to the necessary repeated virtual projections from the image data space into the projection data space and back projections from the projection data space into the image data space and therefore require extremely high-performance hardware.

SUMMARY

At least one embodiment of the present invention is directed to an alternative reconstruction method and a corresponding image reconstruction facility, which produce improved image datasets without requiring a projection data-based iteration using a number of virtual projections and back projections.

At least one embodiment of the present invention is directed to a reconstruction method and at least one embodiment of the present invention is directed to an image reconstruction facility.

At least one embodiment of the present invention is directed to a method for reconstructing an image dataset based on a projection dataset acquired with the aid of an x-ray computed tomography apparatus, the method comprising:

reconstructing a first image dataset based on the projection dataset;

generating an edge image dataset, which indicates a measure of an edge strength of edges occurring in at least one spatial/temporal direction in the first image dataset, as a function of location; and generating an output image dataset based on the first image dataset, with the resolution in the first image dataset being increased as a function of location in at least one spatial/temporal direction taking into account the edge image dataset.

BRIEF DESCRIPTION OF THE DRAWINGS

The invention is described yet again in more detail below with reference to the accompanying figures based on example embodiments.

DETAILED DESCRIPTION OF THE EXAMPLE EMBODIMENTS

Figure 1:
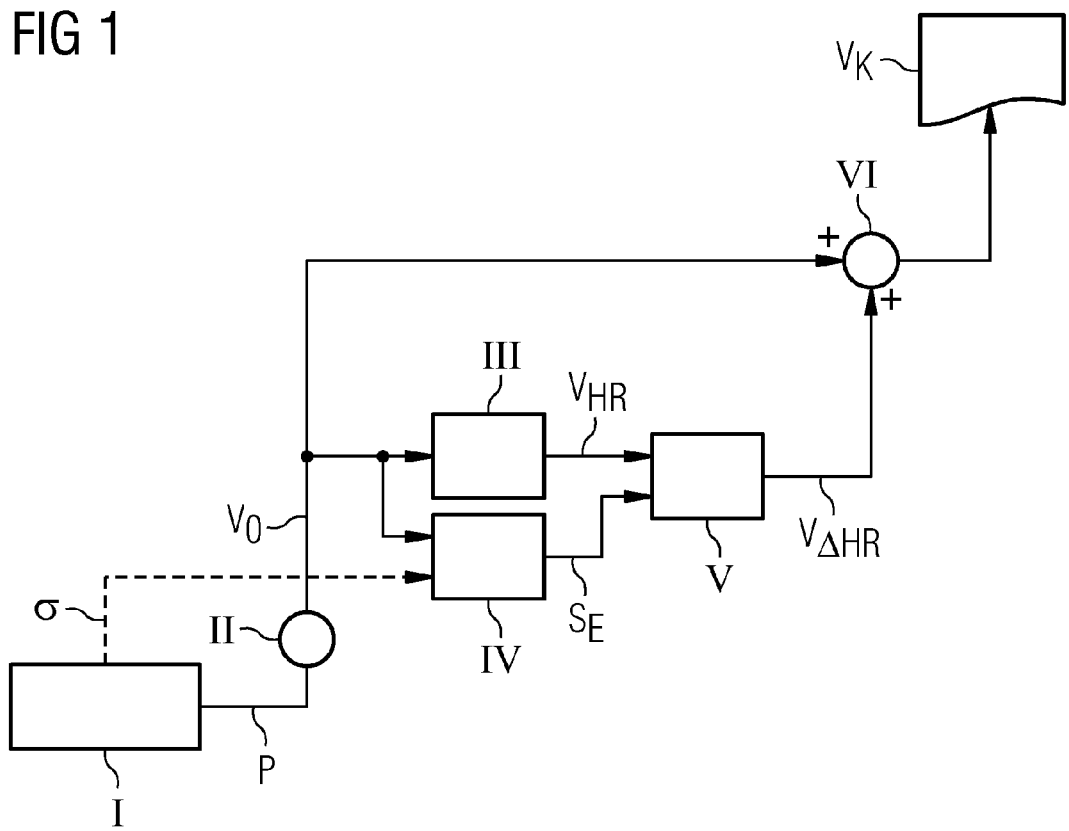
FIG. 1 shows a simplified flow diagram of the possible sequence of a first variant of an embodiment of the inventive method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the method for reconstructing an image dataset based on a projection dataset acquired using an x-ray computed tomography apparatus comprises at least the following method steps:

First a first image dataset is generated based on the projection dataset, which can take place for example in the conventional manner using a simple back projection or the filtered back projection described above.

An edge image dataset is also generated, which indicates a measure of an edge strength of edges occurring in at least one spatial/temporal direction in the first image dataset, as a function of location, in other words with local resolution. This can be done before, at the same time as or after the generation of the first image dataset.

It should be noted here that the image dataset can not only be spatial image data but also image data with a time dimension. For example it can be images of the same slice at different times, as in the manner of a film recording of said slice, or a three-dimensional volume recorded at different times. Four-dimensional image datasets are therefore present in the latter instance. Regardless of whether the image datasets are simply temporally static spatial image datasets or whether they have a time dimension, the space spanned by the spatial and temporal coordinates of the image dataset is referred to in the following as the "image data space" and a "location" is an image point, i.e. a pixel or voxel, within said multidimensional image data space, the position of which is defined by a tuple of the corresponding spatial and temporal coordinate values, e.g. x, y, z and t. The terms "as a function of location" or "with local resolution" therefore also refer to an image point dependency or resolution in a temporal direction, when the image data space has a time dimension. The spatial image dataset (or the spatial part of the image dataset) can be both a collection of slice images, which when viewed together for example cover a specified volume slice by slice, and also true volume data.

According to at least one embodiment of the invention an output image dataset is generated based on this first image dataset, with the resolution in the first image dataset being increased as a function of location in at least one spatial/temporal direction taking into account the edge image dataset. A resolution increase as a function of location here means that there is a different increase in the spatial or in the temporal direction in the temporal resolution locally for different locations in the image data space. The resolution increase is also preferably a function of direction, in other words different in every direction.

With at least one embodiment of the inventive method therefore an "edge-selective" local raising of image sharpness is generally performed in the region of the edges that can be detected in the first image dataset. Since resolution is always associated with a noise increase, such edge-selective raising of the image sharpness has the advantage that the resolution is only increased where it is important, in other words at the edges containing the most important information. This is also more favorable than a general increase in image resolution, since it is possible to accept an increase in noise at the edges where there are greater differences in intensity than in the region of edgeless surface regions, without thereby masking important information.

With an inventive method for generating image data of the interior of an object using an x-ray computed tomography apparatus, as mentioned above the object for which a projection dataset is to be acquired is exposed to x-ray radiation from a number of projection directions. The projection data here can be acquired in a different manner, i.e. using a sequential method and also using a helical method. A reconstruction using the inventive reconstruction method described above is then performed based on the projection dataset. The projection data can be preprocessed first for example. Thus for example the measured projection data can first be filtered once as usual and be stripped of noise as far as possible, after which a rebinning step can also be performed if required. It is also possible here for measured projection data to be interpolated on the basis of actually measured detector projection data. Similarly the projection data can also be subjected beforehand to other correction methods, e.g. beam hardening correction.

A corresponding image reconstruction facility for reconstructing image data according to at least one embodiment of the inventive method must have a measured projection data interface for transferring a projection dataset acquired using an x-ray computed tomography apparatus. The image reconstruction unit also requires a reconstruction unit, which is configured to reconstruct a first image dataset based on the projection dataset. This can be a reconstruction unit, which can generate an image dataset from a projection dataset for example using a conventional back projection method. The image reconstruction facility should also have an edge image dataset generation unit, which is configured so that it generates an edge image dataset during operation, which indicates a location-dependent measure of an edge strength of edges occurring in at least one spatial direction in the first image dataset as a function of location, as well as an image dataset correction unit, which is configured to generate an output image dataset based on the first image dataset, with the resolution in the first image dataset being increased as a function of location in at least one spatial/temporal direction taking into account the edge image dataset. Finally the image reconstruction facility requires an image data interface for outputting the reconstructed image data.

Such an image reconstruction facility can be part of a computed tomography apparatus, in other words it can be installed for example in the conventional manner on a control and evaluation computer of the tomography apparatus. In principle such an image reconstruction facility can however also be implemented in the form of or on another computer unit, which is connected for example to a computed tomography system by way of a network for the transfer of data or can be supplied with corresponding data in a different manner.

In particular the first reconstruction unit, the edge image dataset generation unit and the image dataset correction unit can each be implemented as software modules on a suitable computer with corresponding storage capabilities. The projection data interface and the image data interface can likewise be implemented simply in the form of software, if it is only necessary to transfer measured projection data or to output the image data from or to other further projection data preprocessing units or image data further processing units implemented on the same computer unit. In principle these interfaces can however also be implemented as combined hardware/software interfaces, to implement external inputting and outputting, for example hardware interfaces configured specially with the aid of software components. Outputting of the computed tomography image data here does not only refer to external outputting to a screen, printer or the like but any outputting of the computed tomography image data by the image reconstruction facility, for example storage of the image data for later viewing or further processing in a storage unit. A largely software-based implementation has the advantage that image reconstruction facilities used to date can also be retrofitted in a simple manner by means of a software update, in order to operate in the inventive manner. The object is thus also achieved by a computer program product, which can be loaded directly into a storage unit of a programmable image reconstruction facility, having program segments, in order to execute all the steps of the inventive method, when the program is executed in the image reconstruction facility.

Further advantageous embodiments and developments of the inventive will emerge from the dependent claims and the description which follows. A method or subject matter of one claim category can also be developed here in the same way as the dependent claims of a different claim category.

As mentioned above, the edge image dataset indicates a measure of an edge strength of edges occurring in at least one spatial direction in the first image dataset as a function of location, in other words locally for every image point. This edge strength can be given here in absolute values. However it is preferably ensured when generating the edge image dataset that it indicates a measure of a relative edge strength relative to a local noise strength in the first image dataset. This has the advantage that local noise is also taken into account at the same time in the edge image dataset, which is used to increase image resolution in an edge-selective manner, with for example a smaller resolution increase taking place at the edges where a high noise level is present than at the edges where the noise is only slight in the first image dataset. Local noise strength can be for example the standard deviation of the noise at the respective location in the first image dataset.

To generate the edge image dataset, the first image dataset can preferably be differentiated in at least the relevant spatial/temporal direction. This is one way of identifying edges in the relevant spatial/temporal direction with little computation outlay. It is particularly preferable to this end for example to perform a regularized, i.e. modified and weighted, derivation in the relevant spatial direction. For example to this end a discrete derivative can be convoluted in the respective spatial/temporal direction with any suitable low pass. If, as described above, the edge image dataset is to indicate a relative edge strength relative to the local noise strength, it is only necessary to relate the differential dataset generated during the differentiation of the first image dataset image point by image point to the determined local noise strength.

It is quite particularly preferable for the edge image dataset to be generated in such a manner that the edge strength values at the individual locations of the edge image dataset lie between 0 and a normalized maximum value, preferably 1. This can be achieved simply for example by inserting the determined absolute or (preferably) relative edge strength in a suitable manner into an exponent of a suitable function for calculating the location-dependent edge strength value. This is described in more detail below.

In order to perform the edge-selective image sharpness increase, an image sharpness correction data set is preferably first generated using said edge image dataset. Depending on the local edge strength this contains location-dependent image sharpness correction values, whereby location-dependent is again to be understood in the sense of a location in the multidimensional image data space, which can also comprise a time dimension. The resolution in the first image dataset is then increased by combining the first image dataset with the image sharpness correction data set. Different ways of performing such combining are described in more detail below.

To generate the image sharpness correction dataset for the edge-selective raising of image sharpness, in one preferred variant a second image dataset can first be generated, having an increased resolution in at least one spatial/temporal direction compared with the first image dataset.

This second image dataset can in principle be generated directly from the projection dataset by corresponding interpolation with a suitable convolution kernel or interpolation during the back projection as part of a new reconstruction, e.g. with a different convolution kernel, resulting in a higher resolution. The step for generating the second image dataset can in this instance also be performed parallel to or before the generation of the first image dataset.

However the second image dataset is preferably generated based on the first image dataset. This can be done for example by means of an enhancing interpolation as part of a deconvolution (or convolution) with the first image dataset. A normalized edge-reinforcing filter can preferably be used for the deconvolution for example. The edge-reinforcing filter is preferably selected here in such a manner that during convolution adjacent values of the respectively current image point are taken into account with a negative value, in order thus to generate an anticorrelation, resulting in the resolution and also the noise increase.

This second image dataset can then be combined with the edge image dataset, in order thus to generate the image sharpness correction dataset. To combine the second image dataset with the edge image dataset in this manner, a difference determined image point by image point between the second image dataset and the first image dataset can preferably be multiplied by the edge image dataset, with a weighted multiplication particularly preferably being performed image point by image point. This is a particularly fast and effective method of producing a suitable image sharpness correction dataset, which results selectively in a resolution increase, particularly at points where strong edges occur.

During the generation of the second image dataset with increased resolution, as with the projection data-based iterative reconstruction method mentioned in the introduction, use is made of the fact that the projection data is generally oversampled, in other words more sampling values are present than are actually required to reconstruct the image dataset. The maximum achievable resolution is then determined not by the grid of the detector but by the Nyquist frequency for higher sampling. This oversampling is generally present in the z-direction, i.e. in the advance axis coaxial to the rotation axis of the computed tomography scanner. During a helical scan for example this is due to a small advance between two successive projections compared with the detector grid or during a sequential scan due to the cone angle. Therefore the increase in the resolution in the second image dataset and thus in the first image dataset and accordingly the determination of the edges preferably take place at least in the z-spatial direction. To increase the resolution still further where possible, oversampling can preferably also be increased. To this end during acquisition of the projection dataset a spring focus method with at least two offset focal positions is preferably used.

As mentioned above, a generated image sharpness correction dataset can now be combined in a different manner with the first image dataset, to achieve the desired edge selective image sharpness increase. For example in a particularly simple and fast method this image sharpness correction dataset can simply be added (image point by image point) to the first image dataset, in order thus to obtain the desired improved image dataset.

If a noise reduction is also desired, the first image dataset is preferably also subjected to a noise reduction method. Combining with the image sharpness correction dataset can then take place before such noise reduction, or preferably during it, in other words within the noise reduction method, and/or following the noise reduction method, with simple addition image point by image point also being possible again here.

An iterative noise reduction method has proven to be a particularly effective noise reduction method which still does not require too much computation capacity in the context of the invention, said iterative noise reduction method being purely image data-based, in other words not projection data-based in contrast to the iterative methods mentioned in the introduction. In other words this iterative method takes place solely in the image space. In this process a subsequent iteration image dataset is generated from a current iteration image dataset in each iteration stage, with the image sharpness correction dataset preferably being used in at least one, particularly preferably several, quite particularly preferably even in every iteration stage during a determination of an iteration image dataset from a previous iteration image dataset. It has proven that the noise can be reduced particularly effectively in this manner and at the same time a good edge-selective rise in image sharpness is achieved in a suitable manner, with a certain noise reduction still being achieved even in the edge regions due to interleaving in the iteration method, without again destroying the resolution increase.

During a determination of an iteration image dataset in a current iteration stage from a previous image dataset the image sharpness correction data set, preferably weighted by a weighting factor, is preferably added. This weighting factor can be any positive or negative value. However a predefined number of iteration steps is particularly preferably used in the iteration method and the weighting factor is reciprocally proportional to this predefined number of iteration steps. This means that ultimately in the final output image dataset the values of the image sharpness correction dataset have been added as a maximum once locally to the first image dataset, thereby achieving a local value, which corresponds as a maximum to the image point value in the originally reconstructed first image dataset plus the value determined in the corresponding location in the image sharpness correction dataset.

Alternatively the iteration can also be terminated at the latest after a predefined number of iteration steps or after a predefined convergence criterion has been reached. In this instance a suitable maximum number of iteration steps can also preferably be set and the weighting factor can be determined for example as a function thereof.

It is assumed in the following, simply for greater clarity, that the resolution is only increased in a spatial direction, specifically in the z-direction. However it should be noted specifically that these are only exemplary embodiments and an increase in resolution can also take place in the same manner in other directions including the temporal direction. In other words the specifically proposed method can be generalized to four or even more dimensions, it being possible for the fourth dimension to represent time for example.

The method of an embodiment according to FIG. 1 starts first in step I with a transfer of the projection data, preferably in already preprocessed form. A first image dataset $V_0$ is then generated in a step II. A standard back projection method can be used here. It should however preferably be ensured that no negative statistical correlations are contained in this first image dataset $V_0$, i.e. the autocorrelation function is always $\geq 0$. This is generally the case with standard reconstruction methods, as long as the slice thickness (in the z-direction) is large enough in relation to the width of the detector rows and the convolution kernel, which determines the resolution perpendicular to the z-direction (in the x/y-direction) during the back projection, is not too sharp.

In a step III a second image dataset $V_{HR}$ is generated, which has an increased spatial resolution in at least one direction, here the z-direction, compared with the first image dataset $V_0$. $V_0$ here should preferably be made up such that sampling is high enough that the desired improved resolution is not restricted by the size of the matrix or the basic image point frequency. This basic image point frequency is determined according to the Nyquist theorem by the reciprocal value of double the pixel size, the pixel size being given in units of length. In order to achieve double the resolution for example, the first image dataset $V_0$ could simply be generated in such a manner that two pixels are used for one pixel, by simply interpolating every second pixel in a simple manner or for example inserting the value of an adjacent pixel. It is also preferably ensured that the first image dataset $V_0$ has the same number of image points as the second image dataset $V_{\Delta HR}$.

Since in the present example embodiment the second image dataset $V_{HR}$ is generated by an enhancing interpolation from the first image dataset $V_0$, this is automatic. This resolution increase in the z-direction can be represented mathematically for example in the form $$V_{HR}(x, y, z) = \sum_u G(u) \cdot V_0(x, y, z - u). \tag{1}$$

In equation (1), for the sake of simplicity, only the spatial coordinates (x,y,z) are given, although this should not exclude the possibility of a consideration in respect of a temporal change. In equation (1) the function G(u) is a normalized, edge-reinforcing filter, which is convoluted with the first image dataset $V_0$. u here is the control variable in the z-direction used in the convolution and is included in image point units, i.e. pixels or voxels, in the equation.

The filter G(u) can be defined for example in general form as $$G(u) = \frac{1}{2} \frac{\delta_{u,0} - T(u)}{1 - T(0)}, \quad (2)$$

where T(u) is a normalized low pass filter. $\delta_{u,0}$ is the Kronecker function.

The normalized low pass filter T(u) can be defined for example in the form of a Lorenz function:

$$T(u) = \frac{1}{\pi} \frac{r}{r^2 + u^2} \quad (3)$$

or preferably as Gaussian filter:

$$T(u) = \frac{1}{r\sqrt{2\pi}} \exp\left(-\frac{1}{2}\left(\frac{u}{r}\right)^2\right) \quad (4)$$

In each instance r is a factor, which controls the enhancement range. It is preferably between 0.5 and 2 pixels.

If a Gaussian filter according to equation (4) is used in equation (2), the filter G(u) has the form:

$$G(u) = \frac{1}{b_1}\left(\delta_{u,0} - a_1 \cdot \exp\left(-\left(\frac{u}{r_1}\right)^2\right)\right) \quad (5)$$

The value $b_1$ is a normalization value and is selected such that preferably $$\sum_u G(u) = 1.$$

Figure 2:
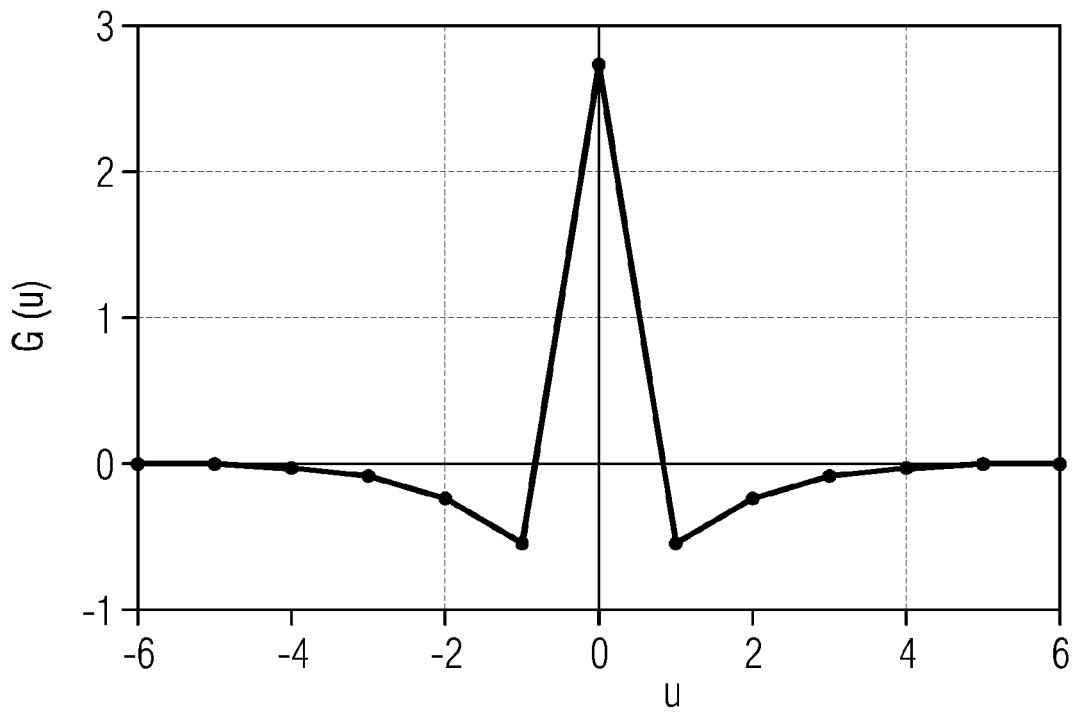
FIG. 2 shows a functional representation of an edge-reinforcing filter for use in an embodiment of an inventive method.

The graph in FIG. 2 shows this function G(u) (in absolute numerical/weighting values) over the variable u (in pixels/voxels) according to equation (5), wherein the values a1=0.2, r1=2, b1=0.291 and u=−6 . . . 6 were used. As shown in this graph, during the convolution the directly adjacent slices are taken into account with a negative value as well as the current slice, in other words they are subtracted in equation (1). The adjacent slices are thus anticorrelated to some degree but the noise is increased, while at the same time the slices are made thinner in each instance and so the resolution is increased.

Also, based on the first image dataset $V_0$, in a step IV (before, parallel to or after step III) an edge image dataset SE is determined. In other words an edge sharpness SE(x,y,z) is calculated, in this instance in the direction of the resolution increase, based on the first image dataset $V_0$. This can advantageously be generated by a general differentiation in the desired direction and a subsequent weight function, This can generally be represented mathematically in the equation $$H(u)=D(u)*T(u), \quad (6)$$

where D(u) is a discrete derivative in the desired spatial direction, here the z-direction, convoluted with any low pass T(u). D(u) can be represented most simply in a matrix notation as follows:

$$D(u)=[-1 0 +1] \quad (7)$$

The low pass T(u) can again be in particular a Lorenz function according to equation (3) or preferably a Gaussian filter according to equation (4). In this instance H(u) can be represented as follows:

$$H(u) = \frac{1}{b_2}\left(u \cdot \exp\left(-\left(\frac{u}{r_2}\right)^2\right)\right) \quad (8)$$

r2 is the range into which the filter extends. It can but does not have to be selected to be identical to the range a of the filter G(u) (see equation (2)). The factor b2 is a normalization value again, which is selected to that the condition $$\sum_u |H(u)| = 1$$

is satisfied. The requirement $$\sum_u H(u) = 0$$

is already satisfied by the structure of H.

Figure 3:
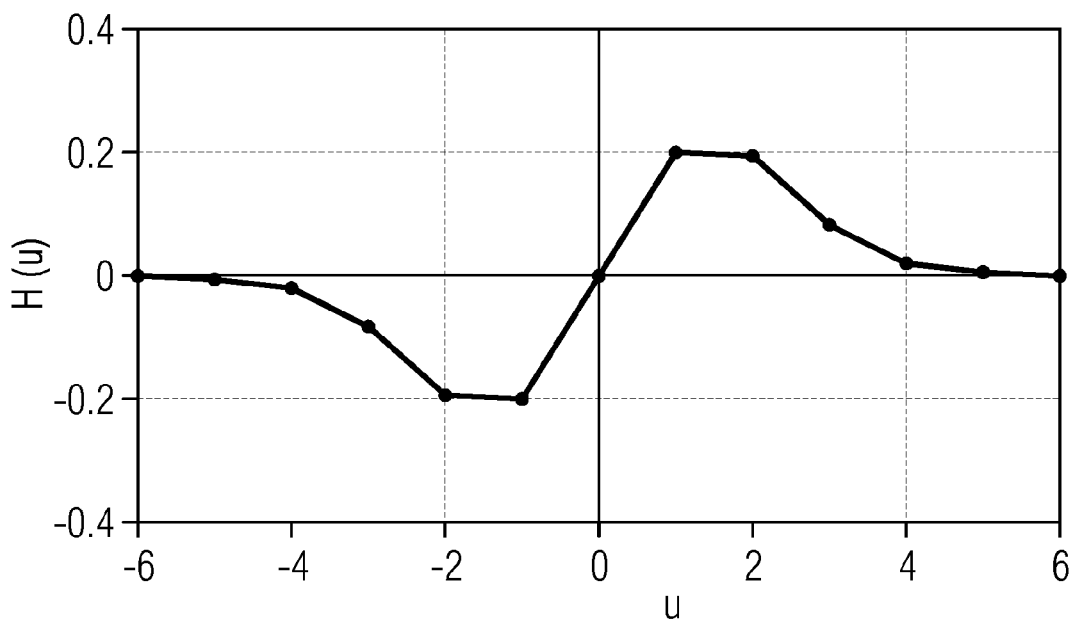
FIG. 3 shows a functional representation of a convolution kernel for determining edge strength for use in an embodiment of an inventive method.

FIG. 3 shows such a suitable function H(u) with the values r2=2, b2=3,829 and u=−6 . . . 6. The value for H(u) is plotted here over u (again in pixels/voxels). A convolution of the first image dataset $V_0$ with this function H(u) according to $$V_E(x, y, z) = \sum_u H(u) \cdot V_0(x, y, z - u) \quad (9)$$

gives a differential dataset $V_E$. This is the result of the modified first derivative in the z-direction, which therefore also indicates, at the individual positions in space (x,y,z), the value of the first derivative in the z-direction and therefore a measure of an edge strength at the respective location. The absolute edge strength thus obtained is however preferably related to a local noise strength σ(x,y,z) to determine the edge image dataset SE. To obtain a normalized edge image dataset SE, a calculation can be made according to $$S_E(x, y, z) = 1 - \exp\left(-\left(\frac{V_E(x, y, z)}{f \cdot \sigma(x, y, z)}\right)^2\right). \quad (10)$$

σ(x,y,z) here is specifically the standard deviation of the noise background present locally at the location (x,y,z). A method for determining this standard deviation directly from the projection data is described for example in Borsdorf et al., "Analytical Noise Propagation for Anisotropic Denoising of CT Images", in: P. Sellin, Ed., 2008, IEEE Nuclear Science Symposium Conference Record, pp. 5335-5338, the entire contents of which are hereby incorporated herein by reference. FIG. 1 shows the use of this local noise standard deviation by means of the broken arrow.

The scale parameter f, which can be preferably between 1 and 5, particularly preferably around 3, allows the edge detection threshold to be set. By calculating the edge image dataset $S_E$ in the form shown in equation (10), it is ensured that the edge image dataset in each instance contains a normalized value between 1 and 0 at the respective locations (x,y,z), which is a function of the edge strength. 1 here is the value for a very reliably identified strong edge and 0 is the value present at locations where no edge was detected. This edge image dataset can thus be used directly for the edge strength-dependent weighting, by simply multiplying said edge image dataset $S_E$ by another image dataset image point by image point.

It is therefore possible in a simple manner in a step V to generate an image sharpness correction dataset $V_{\Delta HR}$ for increasing sharpness in an edge-selective manner based on edge strength according to the following equation, with the aid of the edge image dataset $S_E$:

$$V_{\Delta HR}(x,y,z)=s_E(x,y,z)\cdot[V_{HR}(x,y,z)-V_0(x,y,z)] \quad (11)$$

This image sharpness correction dataset $V_{\Delta HR}$ corresponds to the change between the first, simple image dataset $V_0$, the resolution of which is to be increased, and the image dataset VHR with the increased spatial resolution compared with the first image dataset $V_0$, weighted in each instance image point by image point with the locally present edge strength $S_E$ at the location (x,y,z). The image sharpness correction dataset $V_{\Delta HR}$ thus generated can then simply be added in a step VI to the original first image dataset $V_0$, to generate the desired image dataset $V_K$, which then selectively has increased image sharpness, primarily in the edge region.

Figure 4:
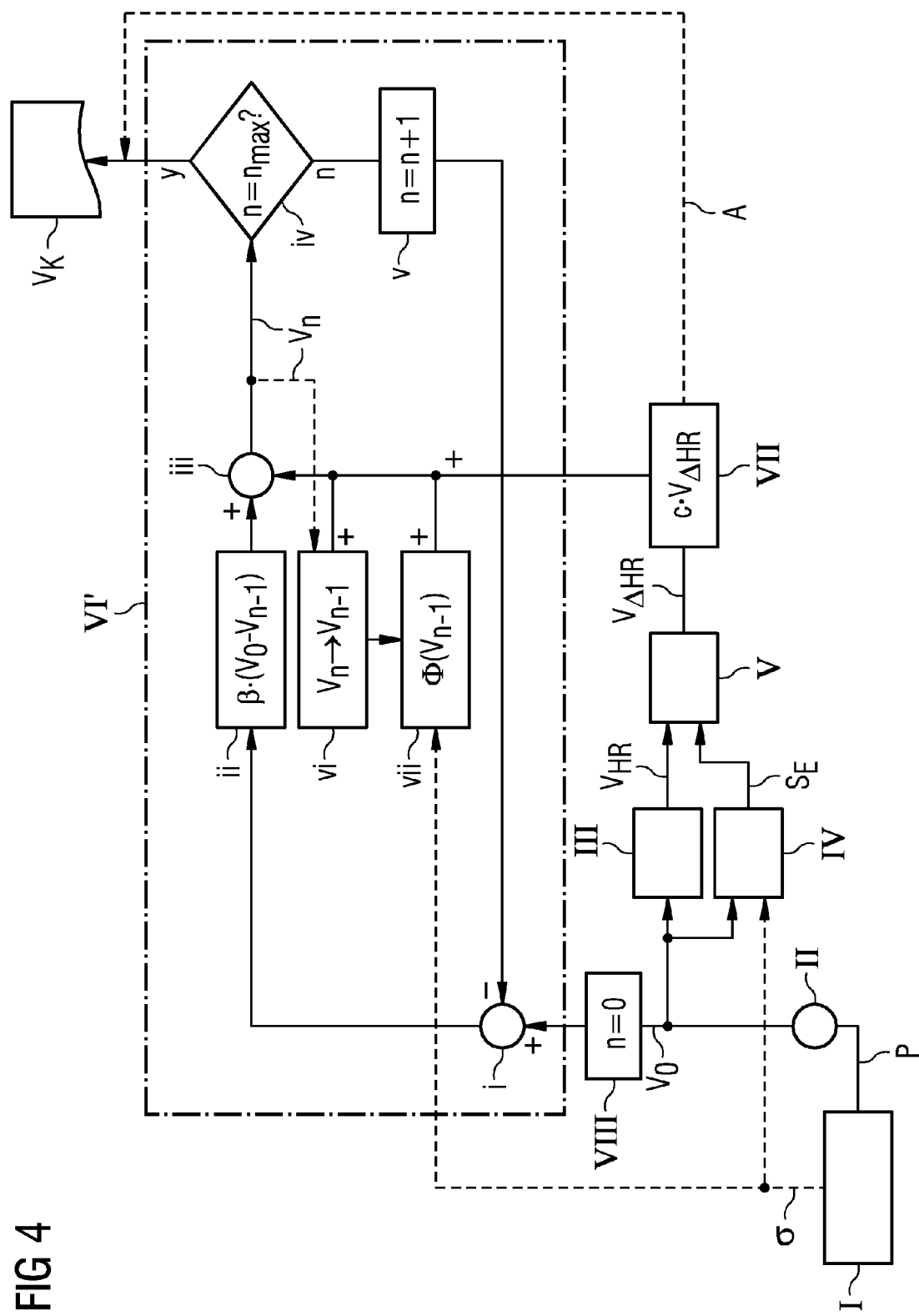
FIG. 4 shows a simplified flow diagram of the possible sequence of a second variant of an embodiment of the inventive method.

With the method illustrated in FIG. 1 it is possible to generate an already much improved image in a very simple manner, since it has been possible to increase the resolution significantly in the region of the important edges, without generally increasing image noise. An even greater improvement can be achieved, if the image dataset is also subjected to a noise reduction method. An iterative noise reduction method can preferably be used here, the iteration only being performed in the image data space. One example of this is illustrated in FIG. 4.

With this method too the projection data P, previously generated by the scanner of the computed tomography apparatus and optionally preprocessed in a suitable manner, is first loaded in step I. A simple back projection also takes place in the conventional manner in step II. This step is no different from the method according to FIG. 1.

The step III for generating a further image dataset $V_{HR}$ based on the first image dataset $V_0$ and the step IV for generating an edge image dataset $S_E$ are also performed in the same manner as in the method according to FIG. 1.

An image sharpness correction dataset $V_{\Delta HR}$ is also generated here again in step V from the edge image dataset $S_E$ and the second image dataset $V_{HR}$, which has an increased resolution in at least one spatial direction compared with the first image dataset $V_0$. However a simple summing of this image sharpness correction dataset $V\Delta HR$ with the first image dataset $V_0$, as in FIG. 1 in step VI, does not then take place but the combining of the image sharpness correction dataset $V_{\Delta HR}$ with the first image dataset $V_0$ takes place as part of an iterative noise reduction in step VI'.

The image sharpness correction dataset $V_{\Delta HR}$ is first multiplied by a weighting factor c to give an input value for this iteration method VI'. This takes place in step VII. The weighting factor c here is preferably selected so that it corresponds to the reciprocal value of the number nmax of the iterations performed as part of the iteration method according to step VI'. The iteration is also prepared for by setting an iteration control variable n=0 in step VIII.

As part of the iteration in every iteration step in a step i the image dataset of a previous iteration step $V_{n-1}$ is subtracted in each instance from the first image dataset $V_0$ (the first image dataset $V_0$ and the further image datasets $V_0$ are also referred to as iteration image datasets in the context of the iteration method). In the first iteration step this "previous" image dataset only contains 0 values, so no subtraction takes place.

The differential image dataset $(V_0-V_{n-1})$ is then multiplied by a regularization factor β in step ii. In step iii the image dataset of the previous iteration step $V_{n-1}$, a regularization value or regularization function $\Phi(V_{n-1})$ and the image sharpness correction dataset $V_{\Delta HR}$ weighted in step VIII with the weighting factor c are then added together, in order thus to generate the current iteration image dataset $V_n$. The corresponding update equation can then be written as follows:

$$V_n=V_{n-1}+\Phi\{V_{n-1}\}+\beta(V_0-V_{n-1})+c\cdot V_{\Delta HR} \quad (12)$$

The regularization function $\Phi(V_{n-1})$ here describes the change to the dataset $V_{n-1}$ derived from the previous image dataset $V_{n-1}$ to calculate the dataset $V_n$. If a diffusion filter is used as the noise reduction method for example, this regularization function would be given as $$\Phi\{V_{n-1}\}(p) = \\ \alpha \cdot \sum_{p'}\left((V_{n-1}(p')-V_{n-1}(p))\cdot\exp\left(-\left(\frac{(V_{n-1}(p')-V_{n-1}(p))}{\sigma(p)}\right)^2\right)\right). \quad (13)$$

In this equation p=(x,y,z) and p' for the sake of simplicity represent a coordinate triplet in space. If the method is used in an image data space, which also includes the time, the time coordinate t would have to be included. The sum passes over the adjacent pixel of p. α here is the width of an iteration step and can assume a value between 0 and 1.

In step iv it is checked whether the number of maximum iteration steps has been reached. If not (branch n), the control variable is increased by 1 in step v and a new iteration pass starts in step i, otherwise (branch y) the current iteration image dataset can be output as the desired improved output image dataset $V_K$. The setting of the number of iterations to a maximum value and the selection of the factor c as a reciprocal value of the maximum number nmax of iterations has the advantage that in the final output image dataset $V_K$ the image point values present in the second image dataset $V_{\Delta HK}$ at the respective image points are added once as a maximum and therefore the value $V_0+V_{\Delta HK}=V_{HR}$ is reached at every location. In other words the resolution of the second image dataset $V_{HR}$ generated in step III is reached as a maximum at the strongest edges.

It should be noted in particular here that as an alternative to the illustrated iterative noise reduction method it is also possible to use any other iterative or even non-iterative noise reduction method. In particular methods can be used, which are used as so-called regularizers in iterative reconstruction methods.

The method described above allows a high resolution increase to be achieved, which corresponds totally to that of raw data-based iterative reconstructions, while suppressing noise at the same time, simply by using standard computed tomography reconstructions, such as filtered image projections and image-based filter steps. The particularly computation-intensive steps, in particular repeated forward and backward projections, are avoided here, so that the method is generally much faster. By evaluating statistical properties on an image dataset with positive autocorrelation functions and processing the spatially increased resolution separately, it is possible to avoid the problem of negative statistical correlations.

Alternatively, instead of taking account of the image sharpness correction dataset $V_{\Delta HR}$ as part of the noise reduction method in step VI' it is also possible to sum the image sharpness correction dataset $V_{\Delta HK}$ (preferably then with the weighting factor c=1) with the noise-reduced image dataset determined using the noise reduction method. This is shown by the broken alternative path A in FIG. 4.

Figure 5:
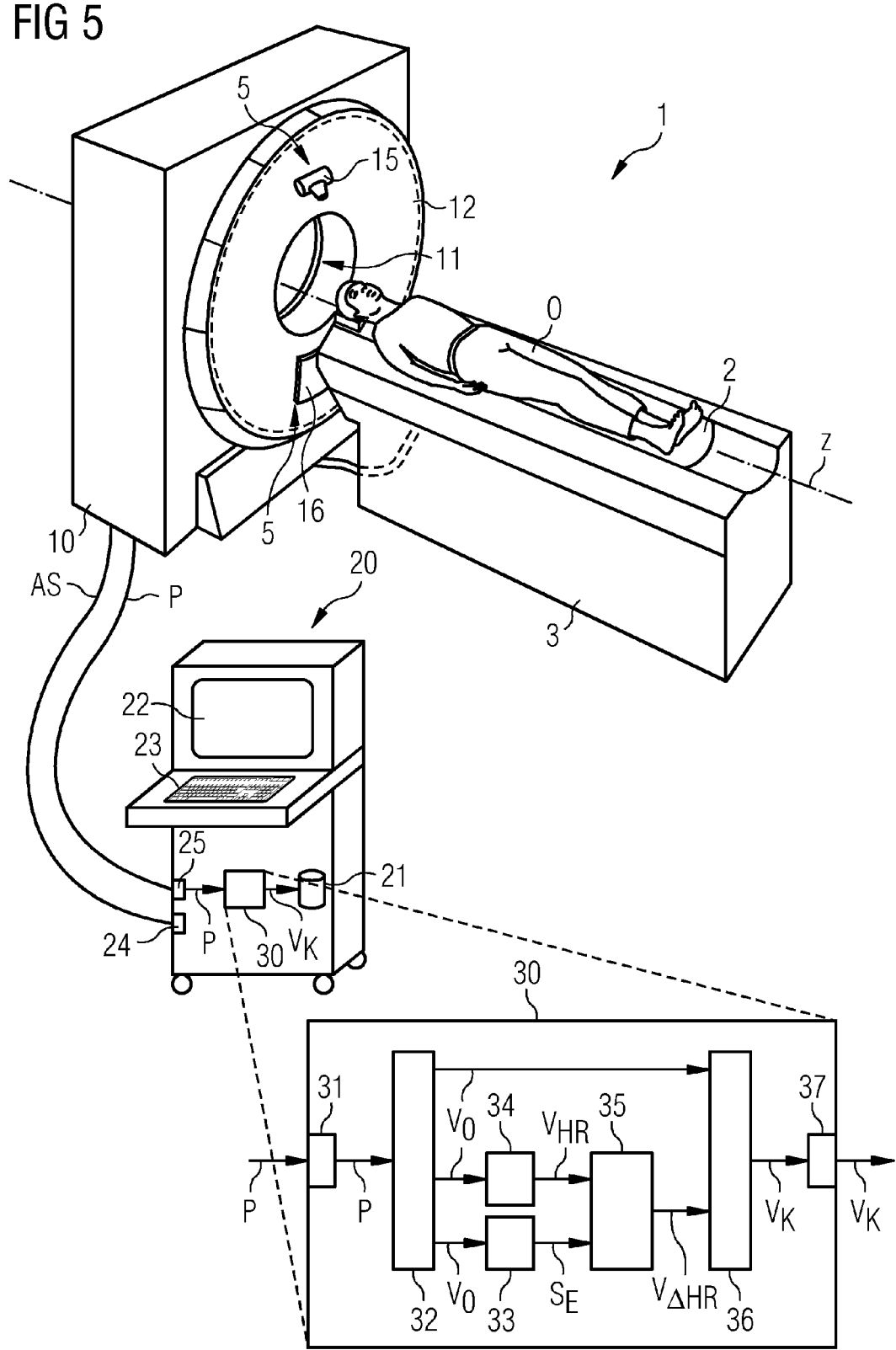
FIG. 5 shows a schematic representation of an example embodiment of a computed tomography system having an image reconstruction facility.

FIG. 5 shows a schematic diagram of a computed tomography apparatus 1 having an inventive image reconstruction facility 30.

The CT apparatus 1 here consists essentially of a standard scanner 10, in which a detector system 5 having a detector 16 and an x-ray source 15 disposed opposite the detector 16 run around a measurement chamber 12 on a gantry 11. Located in front of the scanner 10 is a patient support facility 3 or patient couch 3, the upper part 2 of which can be moved, along with a patient O positioned thereon, toward the scanner 10, in order to move the patient O through the measurement chamber 12 relative to the detector system 16.

The scanner 10 and patient couch 3 are activated by a control facility 20, which emits acquisition control signals AS by way of a standard control interface 24, to activate the entire system in the conventional manner according to predefined measurement protocols. By moving the patient O along the z-direction, which corresponds to the system axis z longitudinally through the measurement chamber 12, and simultaneously moving the x-ray source 15 around, a helical path results for the x-ray source 15 relative to the patient O during the measurement. The detector 16 constantly runs opposite the x-ray source 15 in a parallel manner, to capture projection data, which is then used in the inventive manner to reconstruct volume image data.

A sequential measurement method can also be performed, in which a fixed position is approached in the z-direction and the required measured projection data is then captured during a circuit, a partial circuit or a number of circuits, at the relevant z-position, in order to reconstruct a slice image at said z-position or to reconstruct volume image data from the projection data of a number of z-positions. The inventive method can also be used in principle on other computed tomography apparatuses, e.g. having a number of x-ray sources and/or detectors and/or having a detector forming a complete ring.

The projection data acquired by the detector 16 is transferred to the control facility 20 by way of a measurement data interface 25. Projection datasets P obtained in this manner are then, in some instances after suitable preprocessing, further processed in the manner described above in an image reconstruction facility 30, which in this exemplary embodiment is implemented in the control facility 20 in the form of software on a processor.

The image reconstruction facility here has a projection dataset interface 31 on the input side, which accepts the projection datasets P. A projection dataset P thus read in is then forwarded to a reconstruction unit 32, which uses it to generate the first image dataset $V_0$ as described above for example using a simple filtered back projection method. The image reconstruction facility 30 also has an edge image dataset generation unit 33, which—as also described above—generates an edge image dataset SE based on the first projection dataset $V_0$. The image reconstruction facility 30 also has an image sharpness increasing unit 34, which uses the first image dataset $V_0$ to generate an image dataset $V_{HR}$, which has an increased resolution in at least one spatial direction compared with the first image dataset $V_0$. This method was also described above. Then in a combination unit 35 this second image dataset $V_{HR}$ with increased resolution and the edge image dataset SE are combined in the manner already described, to generate an image sharpness correction dataset $V_{\Delta HR}$. To this extent the unit 35 can also be described as a correction value determination unit 35. The combining of the image sharpness correction dataset $V_{\Delta HR}$ with the original first image dataset $V_0$, as described above, then takes place in an image dataset correction unit 36. In the simplest instance this image dataset correction unit 36 can be structured in such a manner that a simple addition simply takes place here as in step VI according to FIG. 1. However this unit can also be embodied in a more complicated manner, in order for example to perform the combining as part of the noise reduction iteration method according to step VI' in FIG. 4.

The output image dataset $V_K$ ultimately generated by the image dataset correction unit can then be output again by way of an image dataset interface 37.

The output image data $V_K$ reconstructed by the image reconstruction facility 30 can be stored in a storage unit 21 of the control facility 20 and/or be output in the conventional manner on the screen 22 of the control facility 20.

An operator can use this screen 22 and a keyboard 23 or another input unit, such as a mouse or the like (not shown), to operate the computed tomography apparatus 1 and in particular also the image reconstruction facility 30. The projection datasets P and/or the image datasets $V_0$, $V_{HR}$, $V_K$ can also be fed by way of an interface (not shown in FIG. 1) into a network connected to the computed tomography system 1, for example a radiological information system (RIS), and be stored in a mass storage unit that can be accessed there or be output as images on printers or filming stations connected thereto. The data can thus be further processed as required and then stored or output.

The method and reconstruction facility were described primarily with reference to a reconstruction of medical image data. However the invention is not restricted to use in the medical field; computed tomography images can also in principle be generated and processed for other purposes, for example for material testing or the like.

It should finally be noted that the methods and apparatuses described above are simply preferred example embodiments of the invention and the invention can be varied by the person skilled in the art without departing from the scope of the invention, in so far as it is predefined by the claims. In particular the described method is not restricted to the filters, filter facilities and weighting functions used in the examples but other filters and weighting functions with similar properties are also conceivable. Similarly the spatial resolution can be increased in a number of spatial directions and/or in the temporal direction at the same time, which should then be taken into account in the same manner when defining the edge strength, in other words when determining the edge image dataset. Similarly the image data can be reconstructed differently. For example in a sequential method individual slice images can be reconstructed, which are then combined into volume image data or with the helical method volume image data is reconstructed, from which individual slice images can then be generated. For the sake of completeness, it should also be noted that the use of the indefinite article "a" or "an" does not preclude a multiplicity of the relevant features being able to be present. Similarly the term "unit" or "module" does not preclude this consisting of a number of components which can in some instances also be distributed spatially.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing an image dataset based on a projection dataset acquired with the aid of an x-ray computed tomography apparatus, the method comprising:
   reconstructing a first image dataset based on the projection dataset;
   generating an edge image dataset, indicating a measure of an edge strength of edges occurring in at least one spatial/temporal direction in the first image dataset, as a function of location; and
   generating an output image dataset based on the first image dataset, with a resolution in the first image dataset being increased as a function of location in at least one spatial/ temporal direction, taking into account the edge image dataset such that an amount that the resolution of the output image dataset is increased as compared to the first image dataset is less at the edges having a relatively higher noise level than at the edges having a relatively lower noise level.

2. The method of claim 1, wherein the edge image dataset indicates a measure of a relative edge strength relative to a local noise strength.

3. The method of claim 1, wherein to generate the edge image dataset, the first image dataset is differentiated in at least one spatial/temporal direction.

4. The method of claim 1, wherein the edge image dataset is used to generate an image sharpness correction dataset, containing location-dependent image sharpness correction values as a function of the local edge strength, and wherein the resolution in the output image dataset is increased relative to the first image dataset by combining the first image dataset with the image sharpness correction dataset.

5. The method as claimed in claim 4, wherein to generate the image sharpness correction dataset
   a second image dataset is generated with an increased resolution in at least one spatial/temporal direction compared with the first image dataset; and
   the second image dataset is combined with the edge image dataset.

6. The method as claimed in claim 5, wherein to combine the second image dataset with the edge image dataset, a difference between the second image dataset and the first image dataset is multiplied by the edge image dataset.

7. The method as claimed in claim 4, wherein the first image dataset is subjected to a noise reduction method and wherein the combining with the image sharpness correction dataset takes place at least one of during and after the subjecting.

8. The method as claimed in claim 7, wherein the noise reduction method is an iterative noise reduction method, in which in every iteration stage, a current iteration image dataset is used to generate a subsequent iteration image dataset and wherein in at least one iteration stage, the image sharpness correction dataset is used during a determination of an iteration image dataset from a previous iteration image dataset.

9. The method as claimed in claim 8, wherein the image sharpness correction dataset is added during a determination of an iteration image dataset in a current iteration stage from a previous iteration image dataset.

10. The method as claimed in claim 9, wherein during the iteration, a predefined number of iteration steps is used and the weighting factor is reciprocally proportional to the predefined number of iteration steps.

11. A method for generating image data of the interior of an object using an x-ray computed tomography apparatus, the method comprising:
exposing the object, for which a projection dataset is to be acquired, to x-ray radiation from a number of projection directions; and
reconstructing an image dataset from the projection dataset using the method of claim 1.

12. The method as claimed in claim 11, wherein a spring focus method is used to generate the projection dataset.

13. An image reconstruction device for reconstructing an image dataset of an object, comprising:
a processor and a memory, the memory containing computer readable code that, when executed by the processor configures the processor as,
a projection dataset interface, configured to transfer a projection dataset acquired with the aid of an x-ray computed tomography apparatus;
a first reconstruction unit, configured to reconstruct a first image dataset based on the projection dataset;
an edge image dataset generation unit, configured to generate an edge image dataset, which indicates a measure of an edge strength of edges occurring in at least one spatial/temporal direction in the first image dataset, as a function of location;
an image dataset correction unit, configured to generate an output image dataset based on the first image dataset, with a resolution in the first image dataset being increased as a function of, location in at least one spatial/temporal direction taking into account the edge image dataset such that an amount that the resolution of the output image dataset is increased as compared to the first image dataset is less at the edges having a relatively higher noise level than at the edges having a relatively lower noise level; and
an image data interface, configured to output the output image dataset.

14. An x-ray computed tomography apparatus comprising:
an x-ray source and a detector system, for acquiring a projection dataset of an object; and
the image reconstruction device of claim 13.

15. A non-transitory computer readable medium storing a computer program product, directly loadable into a storage unit of a programmable image reconstruction device, including program code segments, to execute the method of claim 1, when the program is executed in the image reconstruction device.

16. The method of claim 2, wherein to generate the edge image dataset, the first image dataset is differentiated in at least one spatial/temporal direction.

17. The method as claimed in claim 5, wherein the first image dataset is subjected to a noise reduction method and wherein the combining with the image sharpness correction dataset takes place at least one of during and after the subjecting.

18. The method as claimed in claim 6, wherein the first image dataset is subjected to a noise reduction method and wherein the combining with the image sharpness correction dataset takes place at least one of during and after the subjecting.

19. The method as claimed in claim 9, wherein the image sharpness correction dataset is weighted by a weighting factor and is added during the determination of an iteration image dataset in a current iteration stage from a previous iteration image dataset.

20. A non-transitory computer readable medium including program segments for, when executed on a computer device, causing the computer device to implement the method of claim 1.

21. A method for reconstructing an image dataset based on a projection dataset acquired with the aid of an x-ray computed tomography apparatus, the method comprising:
reconstructing a first image dataset based on the projection dataset;
generating an edge image dataset, indicating a measure of an edge strength of edges occurring in at least one spatial/temporal direction in the first image dataset, as a function of location;
generating a second image dataset with an increased resolution in at least one spatial/temporal direction compared with the first image dataset;
generating an image sharpness correction dataset by combining the second image dataset and the edge image dataset, the image sharpness correction data set containing location-dependent image sharpness correction values as a function of the local edge strength; and
generating an output image dataset by combining the first image dataset with the image sharpness correction dataset, with a resolution in the first image dataset being increased as a function of location in at least one spatial/temporal direction, taking into account the edge image dataset.

* * * * *